United States Patent [19]

Küffner et al.

[11] 4,204,867
[45] May 27, 1980

[54] PROCESS FOR THE PRODUCTION OF COLOR PHOTOGRAPHIC IMAGES USING NEW WHITE COUPLER SUBSTANCES

[75] Inventors: Karl Küffner, Unterhaching; Wolfgang Lässig; Ernst Meier, both of Munich; Immo Boie, Cologne; Gertrud Kirchhoff, Leverkusen; Helmut Häseler, Leverkusen; Herbert Stark, Leverkusen, all of Fed. Rep. of Germany

[73] Assignee: Agfa-Gevaert Aktiengesellschaft, Leverkusen, Fed. Rep. of Germany

[21] Appl. No.: 876,701

[22] Filed: Feb. 10, 1978

[30] Foreign Application Priority Data

Feb. 12, 1977 [DE] Fed. Rep. of Germany ....... 2705974

[51] Int. Cl.$^2$ ............................................. G03C 7/00
[52] U.S. Cl. .................................. 430/376; 430/3 80; 430/566; 430/577
[58] Field of Search ................... 96/100, 95, 56.3, 56.5

[56] References Cited

U.S. PATENT DOCUMENTS

| | | | |
|---|---|---|---|
| 2,126,337 | 8/1938 | Mannes et al. | 96/56.3 |
| 2,395,846 | 3/1946 | Carroll et al. | 96/126 |
| 2,421,693 | 6/1947 | Harriman | 96/56.5 |
| 4,052,213 | 10/1977 | Credner et al. | 96/95 |
| 4,059,447 | 11/1977 | Meier et al. | 96/100 R |

Primary Examiner—J. Travis Brown
Attorney, Agent, or Firm—Connolly & Hutz

[57] ABSTRACT

White couplers which are capable of reacting with color developer oxidation products to form colorless end product with the consumption of four oxidation equivalents and which, therefore have increased absorption capacity for color developer oxidation products correspond to the formula

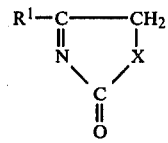

or its tautomeric form, in which $R^1$ is hydrocarbyl, heterocyclyl attached through a ring carbon, or $-CO-R^2$ $R^2$ is alkyl, aryl, alkoxy, amino X is $-S-$ or $-NR^3-$ $R^3$ is hydrogen, same as represented by $R^1$ or an electron-attaching group.

The four-equivalent white couplers may be contained in processing solutions or, in diffusion resistant form, in one or more layers of a colorphotographic material.

2 Claims, No Drawings

PROCESS FOR THE PRODUCTION OF COLOR PHOTOGRAPHIC IMAGES USING NEW WHITE COUPLER SUBSTANCES

This invention relates to a process for the production of colour photographic images by the chromogenic development of photographic materials comprising silver halide emulsion layers and colour couplers incorporated in non-diffusing form, in which colour reproduction and image quality are improved by the use of new white coupler compounds.

It is known that the colour reproduction of colour photographic materials can be improved by using so-called white couplers (as described by W. Püschel, "Zur Chemie der Weisskuppler", Mitteilungen aus den Forschungslaboratorien der Agfa-Gevaert AG, Leverkusen-Munchen, Vol. IV, 1964, pages 352 et seq). The effect of these white couplers is based on the fact that they react with the oxidation product of the colour developer to form colourless compounds. Accordingly, they are best used in cases where it is desired to intercept undesired developer oxidation products in order to prevent any deterioration in image quality. For example, the diffusion of oxidised colour developer from one colour layer into adjacent colour layers and, hence, undesirable co-coupling in the adjacent layers can be prevented by means of non-diffusing white couplers incorporated into intermediate layers. In addition, favourable effects improving graininess and sharpness can be obtained by adding soluble white couplers as so-called competing couplers to the colour developer. In bleaching or bleach-fixing baths, the addition of white couplers prevents the formation of colour fogs from colour coupler by colour developer entrained from the developer bath which is oxidised in the bleaching bath and is hence rendered couplable. This is particularly important when only brief, if any, rinsing with water is carried out between the developer bath and the following oxidising bleaching bath.

In the past, the white couplers generally used have been compounds of the type derived from conventional colour couplers in that they contain, as substituent in the coupling site, an organic radical which is not released or eliminated during or in consequence of the reaction with the oxidation product of the colour developer, so that the reaction of the white coupler with the developer oxidation product has to stop at the stage of the colourless leuco compound. In the most simple case, the substituents in the coupling site may be alkyl, cycloalkyl or aralkyl radicals. Thus, German Pat. No. 1,155,675 describes white couplers which are primarily derived from conventional magenta couplers and yellow couplers, resp. essentially by the fact that the corresponding pyrazolones or open-chain ketomethylene compounds contain in the coupling site an alkyl radical which cannot be released during the colour coupling reaction.

A common feature of all hitherto known white couplers is that they are able to bind one mole of colour developer oxidation product per mole of white coupler and hence require two equivalents of silver halide for the reaction. Accordingly, they may be regarded as two-equivalent couplers.

In contrast to dye-producing colour couplers, in the case of which it is desirable to produce as much dye as possible with at little silver halide as possible and in the case of which, therefore, an improvement is seen in the changeover from the four-equivalent couplers unsubstituted in the coupling site to the two-equivalent couplers carrying a releaseable substituent in the coupling site, white couplers which are of course intended to arrest and neutralise excess developer oxidation product are required to show a particularly high absorption capacity for this developer oxidation product. However, all hitherto known white couplers are only able to bind one molecule of developer oxidation product and hence only two oxidation equivalents per coupling site. Accordingly, the object of the present invention is to find white couplers which have an increased absorption capacity for developer oxidation products.

New compounds have now been found which are distinguished by the fact that they react with the oxidation product of colour developer compounds containing at least one primary aromatic amino group using up four oxidation equivalents to form colourless end products. Under the conditions of photographic development, deep blue to purple coloured azomethine dyes are formed as intermediate stages during this reaction, although they are unstable and decompose spontaneously in the alkaline medium of the developer, becoming colourless in doing so.

The present invention relates to a process for the production of coloured images by the chromogenic development of an imagewise exposed colour photographic material comprising at least one silver halide emulsion layer with which a non-diffusing colour coupler is associated, comprising (at least) the processing steps of colour development, bleaching and fixing.

In the process according to the invention, the colour development step and/or the bleaching step is or are carried out in the presence of a compound which reacts with colour developer oxidation products using up four oxidation equivalents to form colourless end products. Accordingly, the invention provides completely new coupler compounds, namely coupler compounds which, during coupling with developer oxidation products, use up four oxidation equivalents without at the same time forming coloured end products. The coupler compounds in question are white couplers showing an increased absorption capacity for developer oxidation products (four-equivalent white couplers). Compounds showing the properties according to the invention are, for example, 1,3-thiazolinones-2 and imidazolinones-2 which are unsubstituted in the 5-position and which carry in the 4-position any photographically inert substituent attached through a carbon atom. Compounds such as these may be represented by the following general formula I or its tautomeric form Ia:

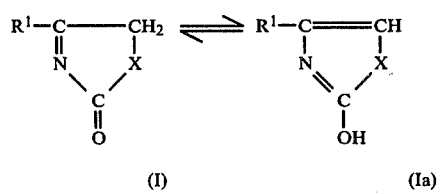

(I)                (Ia)

in which
$R^1$ represents a hydrocarbyl radical a heterocyclic group attached through a ring carbon atom or a group —CO—$R^2$
where $R^2$ represents an alkyl, aryl or alkoxy group or an amino group including a cyclic amino group which may be substituted by alkyl or aryl;

X represents —S— or —NR$^3$—
where R$^3$ represents hydrogen or one of the radicals defined under R$^1$ or, preferably, an electron-attracting substituent, such as —CN, an alkoxycarbonyl radical, a carbamoyl radical, a sulphamoyl radical or an alkyl or aryl sulphonyl radical. A hydrocarbyl radical is an aliphatic or aromatic hydrocarbon radical, for example an alkyl or aryl radical which may be substituted.

Examples of aliphatic hydrocarbon radicals, which R$^1$ to R$^3$ may represent, are alkyl groups containing from 1 to 18 carbon atoms which may be linear, branched or cyclic and which may be substituted for example by alkoxy, aroxy, aryl, halogen, carboxy or sulpho groups, such as methyl, isopropyl, tert.-butyl,-dodecyl, heptadecyl, benzyl, phenethyl, carboxy-tert.-butyl and methoxypropyl.

Examples of aromatic groups, which R$^1$ and R$^3$ may represent, are phenyl and naphthyl groups which may be substituted by one or more substituents, for example by alkyl, alkoxy, alkylamino, dialkylamino or alkyl thio in which the alkyl radicals may contain from 1 to 20 carbon atoms; halogen, such as chlorine or bromine; carboxy, sulpho, nitro, cyano; acyl or acylamino in which the acyl groups are derived from aliphatic or aromatic carboxylic or sulphonic acids, including carbamic acids and sulphamic acids which may be substituted.

The following are examples of substituted aromatic groups: sulphophenyl, sulphonaphthyl, ω-sulphopropoxy phenyl, tetradecoxy phenyl, dodecyl phenyl, t-butyl phenyl, tetradecanoyl aminophenyl, hexadecylthio phenyl, α-(2,4-di-t-pentylphenoxy)-butyramidophenyl, 2-tetradecyl-4-chloro-5-methyl phenoxy ethoxy carbonyl aminophenyl, 2,4-di-t-pentyl phenoxy acetylaminophenyl, α-sulphostearoylaminophenyl, 3-pentadecyl phenoxyethoxy carbonyl aminophenyl, 4-(1-octadecyl-5-sulphobenzimidazolyl-2-phenyl, 2-N-methyl-N-octadecylamino-5-sulphophenyl, N-phenyl-N-octadecyl sulphamoyl phenyl, tetradecyl sulphonyl phenyl, 2-tetradecoxy-5-N-methyl sulphonyl phenyl, dimethylaminosulphonyl phenyl, ethyl-N-octadecyl carbamoyl phenyl, N-phenyl carbamoyl phenyl, 4-(α-carboxymethyl)-phenyl, 4-(α-carboxymethoxy)-phenyl, 3-(α-carbethoxymethyl)-phenyl, 2-(α-tert.-butyloxycarbonylmethyl)phenyl, 4-(α-carboxy-α-dodecylmethoxy)-phenyl, 4-(α-carboxy-α-octylmethyl)-phenyl, 3-(α-dodecyloxycarbonylmethoxy)-phenyl, 4-[α-(o-tetradecyloxyphenylcarbamoyl)-methyl]-phenyl, 4-(α-carboxy-N-methylamino)-phenyl, 3-(α-sulphomethyl)-phenyl.

One group which is particularly suitable as an example of an aromatic group represented by R$^3$ is the group:

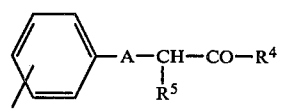

in which
A represents a single chemical bond or an intermediate member such as —O—, —S— or —NR'—, where R' is hydrogen or alkyl;
R$^4$ represents a hydroxy, alkoxy, alkylamino or arylamino group and R$^5$ represents hydrogen or an alkyl group preferably with 1 to 16 carbon atoms.

Examples of heterocyclic groups which R$^1$ and R$^3$ may represent are 5 or 6-membered heterocyclic radicals, preferably heteroaromatic radicals, for example pyridyl, thienyl, thiazolyl, furanyl or indole radicals.

Under a cyclic amino group which may be represented by R$^2$ we understand in particular a heterocyclic group containing at least one nitrogen atom and having at that nitrogen an exocyclic valence bond through which it may be connected to the —CO— group; examples of such cyclic amino groups are pyrrolidino, piperidino, morpholino, thiomorpholino, N'-alkyl-1,4-diazino and dihydroindole groups.

The four-equivalent white coupler compounds according to the invention may either be soluble and diffusible in photographic processing baths or alternatively may be incorporated in diffusion resistant form in colour photographic materials. In the first case, they preferably contain at least one solubilising group, for example at least one sulpho-group, and are largely free from diffusion-preventing radicals. If on the other hand they are to be incorporated in non-diffusing form in the layers of the colour photographic material, the compounds according to the invention contain at least one diffusion-preventing radical.

Diffusion-preventing radicals may be regarded as radicals which make it possible for the compounds according to the invention to be incorporated in diffusion-resistant form in the hydrophilic colloids normally used in photographic materials. Preferred radicals of this type are organic radicals which may generally contain linear or branched aliphatic groups and, may also contain isocyclic or heterocyclic aromatic groups. The aliphatic portion of these radicals generally contains from 8 to 20 carbon atoms. These radicals are attached to the rest of the molecule either directly or indirectly, for example through one of the following groups: —CONH—, —SO$_2$NH—, —CO—, —SO$_2$—, —O—, —S— or —NR'—, in which R' is hydrogen or alkyl.

In addition, the diffusion-preventing radical may also contain water-solubilising groups, such as for example sulpho groups or carboxyl groups, which may be present in anionic form. Since the diffusion property is dependent upon the molecular size of the total compound used, it is sufficient in certain cases, for example when the total molecule used is large enough, to use one or more relatively short chain radicals, such as t-butyl, cyclopentyl or isoamyl radicals, as the diffusion-preventing radicals.

In the case of 1,3-thiazolinone(-2) compounds (X=S) to be incorporated in diffusion-resistant form, the diffusion-preventing radical is situated in the 4-position in the substituent R$^1$. In the case of the imidazolinone compounds (X=NR$^3$), there is a further possibility of introducing the diffusion-preventing radical into the substituent R$^3$ in addition to the substitution in the 4-position.

Examples of four-equivalent white couplers which may be used in accordance with the invention are given in the following.

A. Soluble compounds
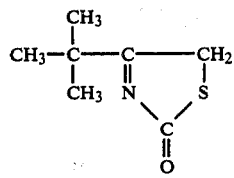 1.
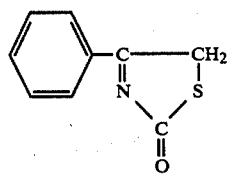 2.
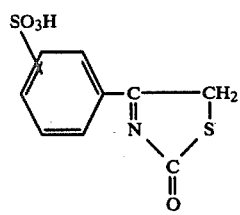 3.
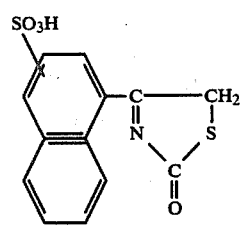 4.
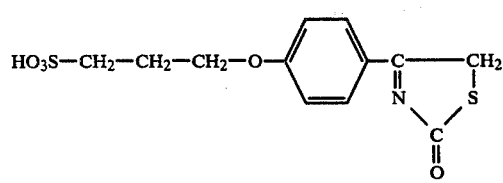 5.
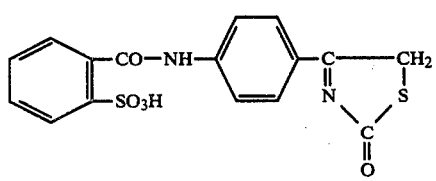 6.
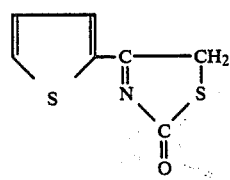 7.
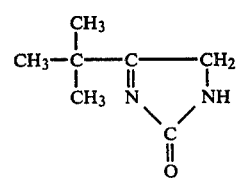 8.
-continued
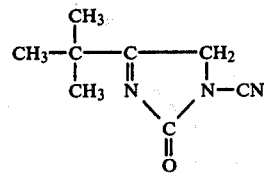 9.
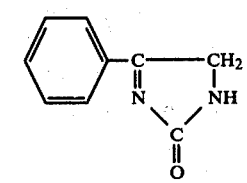 10.
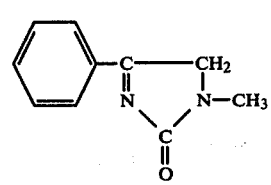 11.
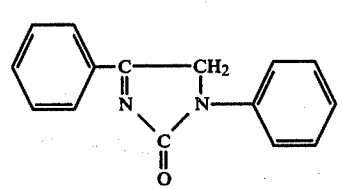 12.
13.
14.
15.
16.

17. 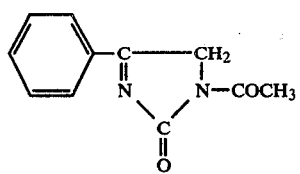
18. 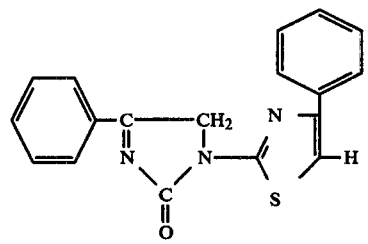
19. 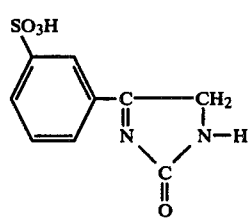
20. 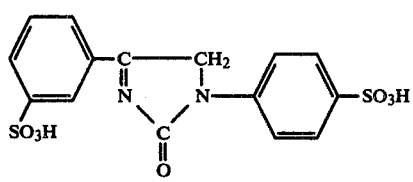
21. 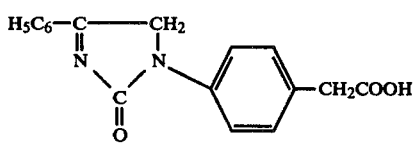
22. 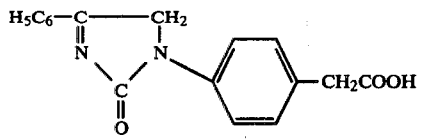
23. 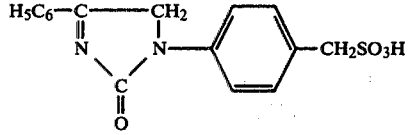
24. 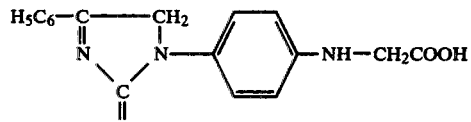
25. 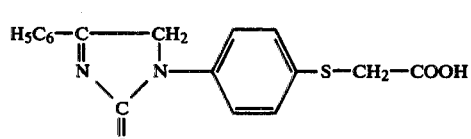
26. 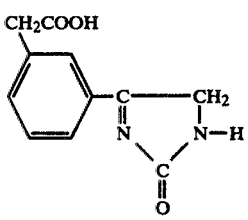
Non-diffusing compounds:
27. 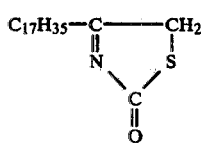
28. 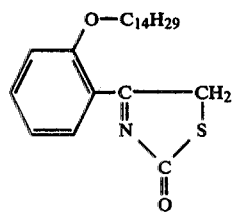
29. 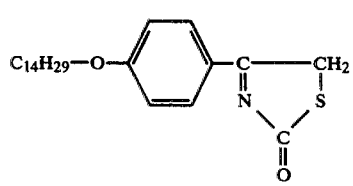

-continued
30.
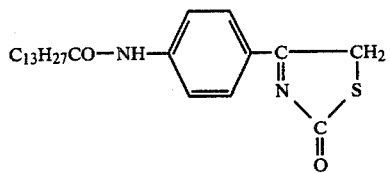
31.
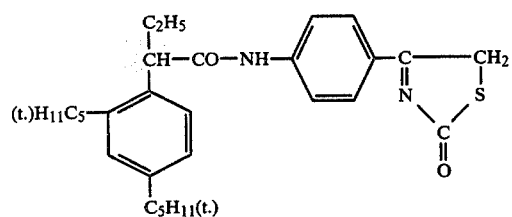
32.
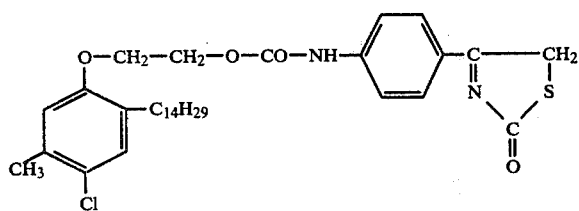
33.
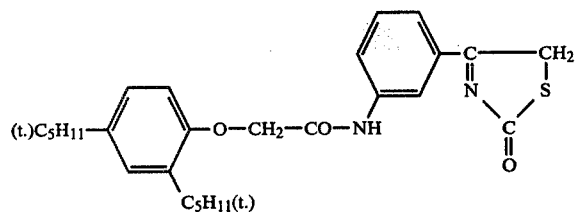
34.
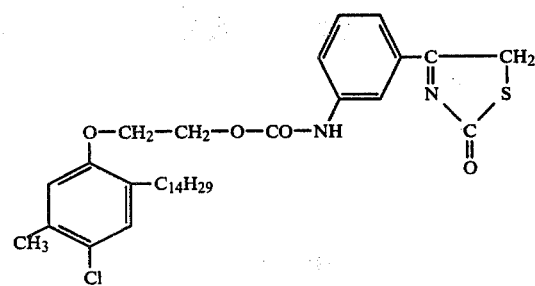
35.
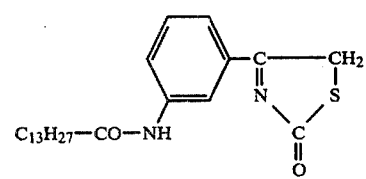
36.
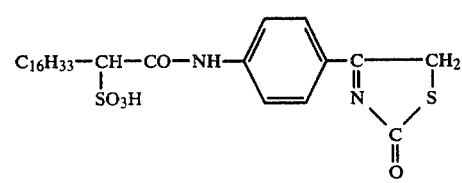

-continued
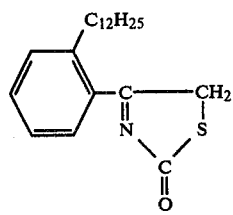
37.
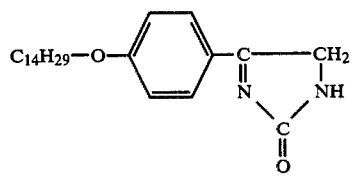
38.
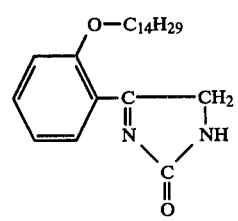
39.
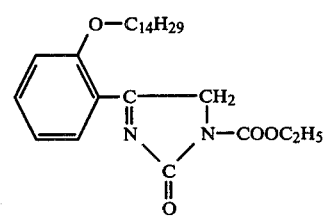
40.
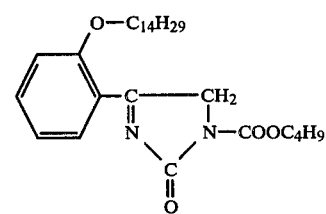
41.
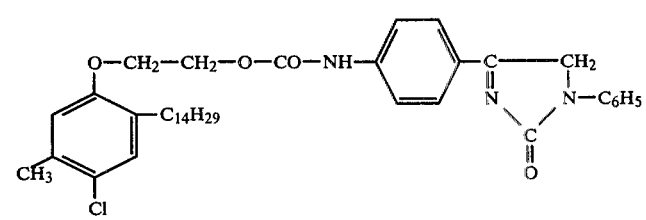
42.
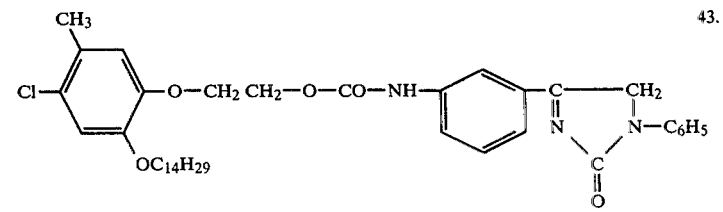
43.

-continued
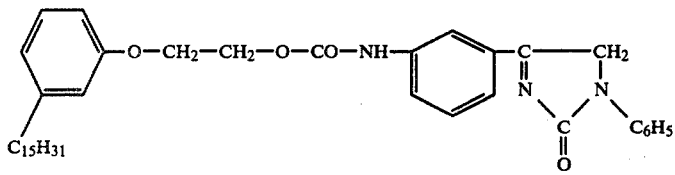 44.
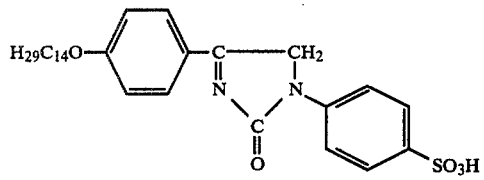 45.
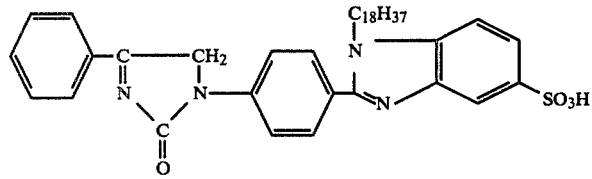 46.
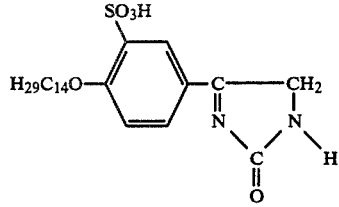 47.
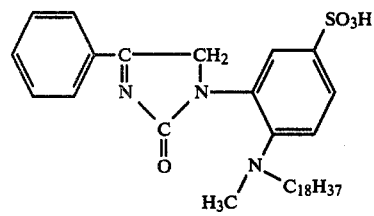 48.
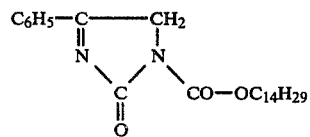 49.
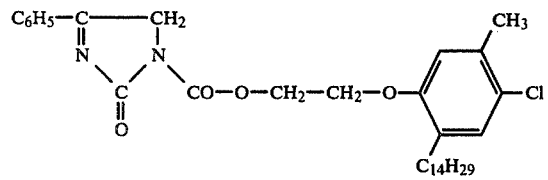 50.
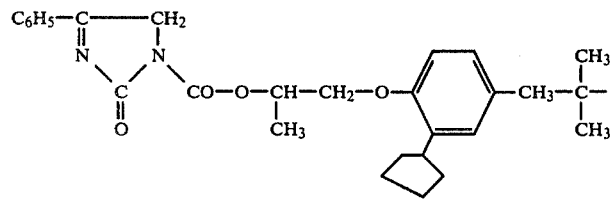 51.

-continued
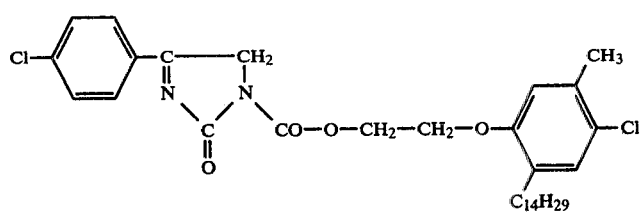
52.
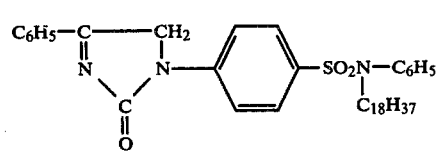
53.
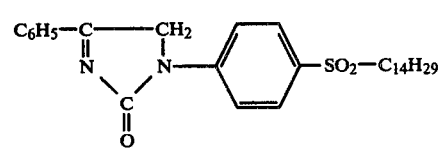
54.
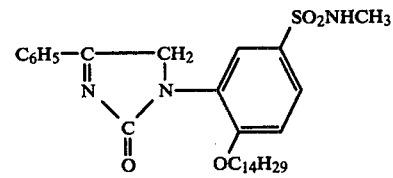
55.
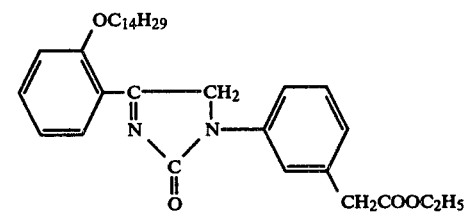
56.
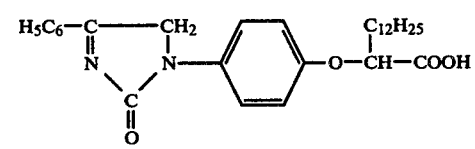
57.
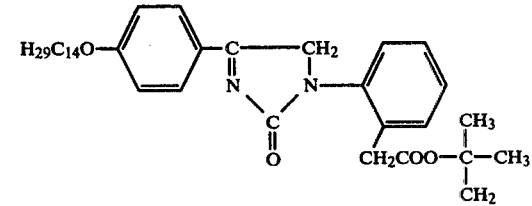
58.
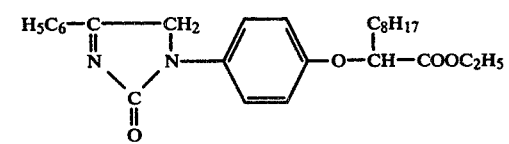
59.
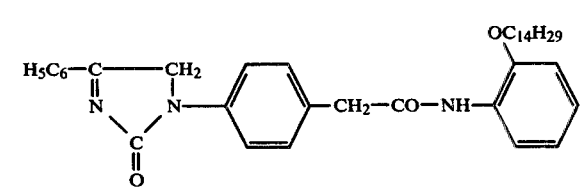
60.

-continued

61.
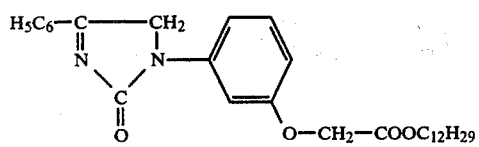

62.
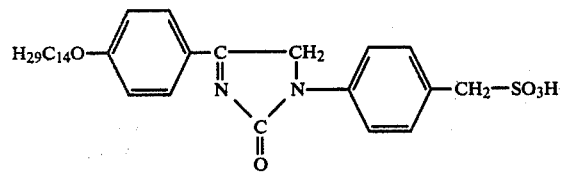

63.
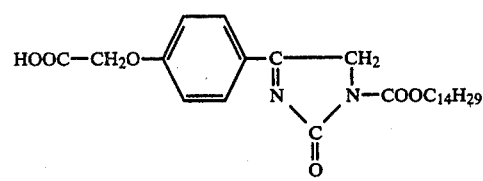

64.
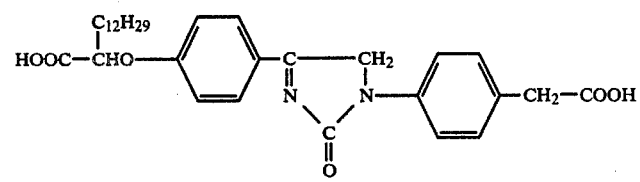

For producing the compounds according to the invention corresponding to general formula I, in which X=S, suitable halogen ketones II are reacted in alcoholic solution with KSCN to form the thiocyano compounds III. The thiocyanogen compounds III may then be cyclised in approximately 90% glacial acetic acid under the catalytic influence of $H^+$-ions (sulphuric acid) to form the 2-hydroxy-1,3-thiazole compound Ia:

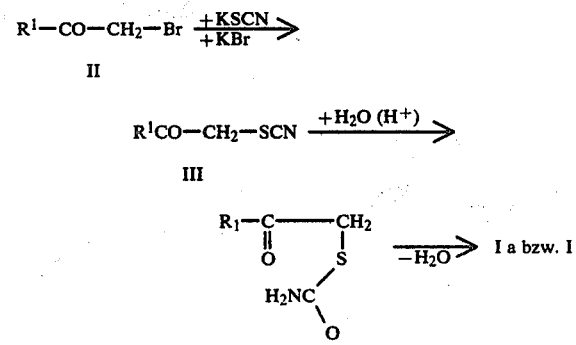

The synthetic process differs according to the nature of the substituent $R^1$, as illustrated by the following examples:

Production of compound 2:

150 g of ω-chloroacetophenone are dissolved at 50° C. in 1000 ml of ethanol, followed by the addition of a solution of 102 g of KSCN in 40 ml of water. After stirring for 10 minutes at 50° C., the ω-thiocyano acetophenone formed is precipitated with water.

Yield: 160 g; m.p. 74°–75° C.

160 g of ω-thiocyano acetophenone are dissolved at 75° C. in 650 ml of glacial acetic acid, followed by the addition of a solution of 13 ml of concentrated sulphuric acid in 85 ml of water. The mixture undergoes spontaneous heating to boiling point. It is then boiled under reflux for about another 20 minutes and left to cool. The deposit precipitated is filtered off under suction and is recrystallised once more from glacial acetic acid.

Yield: 103 g; m.p. 207°–209° C.

Production of compound 3:

25 g of 2-hydroxy-4-phenyl-1,3-thiazole (compound 2) are dissolved in 140 ml of concentrated sulphuric acid. 61.5 ml of fuming sulphuric acid (D=1.98) are added dropwise while cooling with ice and the mixture is slowly brought to room temperature. It is then poured into ice and the excess sulphuric acid is precipitated in the form of barium sulphate by adding an aqueous solution of approximately 900 g of barium chloride. The deposit is filtered off hot. Concentration of the filtrate gives 12 g of compound 3. m.p.: above 300° C.

Production of compound 6

330 g of 4-nitroacetophenone are dissolved at 40° C. in 600 ml of glacial acetic acid and brominated by the dropwise addition of a solution of 103 ml of bromine in 200 ml of glacial acetic acid. The mixture is then stirred for 30 minutes at 40° C. and cooled. Yellow crystals melting at 99° to 101° C. are precipitated. Yield: 273 g.

244 g of ω-bromo-4-nitroacetophonone are dissolved at 55° C. in 1000 ml of ethanol, followed by the dropwise addition of a solution of 98 g of KSCN in 100 ml of water. After stirring for 30 minutes at 60° C., the thiocyano compound is precipitated with water.

Yield: 205 g; m.p. 116°–117° C.

222 g of ω-thiocyano-4-nitroacetophenone are dissolved hot in 900 ml of glacial acetic acid, followed by the addition of a solution of 28 ml of concentrated sulphuric acid in 110 ml of water. The mixture is then heated for 2 hours on a steam bath. 2-Hydroxy-4-p-nitrophenyl-1,3-thiazole precipitates on cooling in the form of yellow needles. Filtration under suction and washing with glacial acetic acid gives 165 g, m.p. 311°–313° C.

58 g of 2-hydroxy-4-p-nitrophenyl-1,3-thiazole are introduced in portions with stirring at 70° C. into a solution of 233 g of $SnCl_2.2\ H_2O$ in 1025 ml of concentrated hydrochloric acid. The mixture is then left to react out for about 30 minutes at 80° C. and is subsequently cooled. The deposit precipitated is filtered off under suction. Yield of 2-hydroxy-2-p-aminophenyl-1,3-thiazole hydrochloride: 67 g, m.p.: 211°–226° C.

The free amine is obtained by dissolution in 1 n NaOH and reprecipitation with glacial acetic acid.

19 g of 2-hydroxy-4-p-aminophenyl-1,3-thiazole are dissolved hot in 200 ml of pyridine, followed by the addition of 18.5 g of benzoic acid-2 sulphonic acid anhydride. After heating under reflux for 10 minutes, most of the pyridine is removed in a vacuum rotary evaporator and the residue is taken up in 30% acetic acid. Compound 6 crystallises out. Yield: 17 g; m.p.: 277°–285° C. with decomposition.

Production of compound 30

65 g of 2-hydroxy-4-p-aminophenyl-1,3-thiazole are dissolved warm in 700 ml of pyridine, followed by the slow dropwise addition of 70.5 g of myristic acid chloride. The reaction is exothermic. After reaction for 2 hours at 60° C., the reaction mixture is poured onto dilute hydrochloric acid. The deposit precipitated is filtered off under suction and recrystallised from glacial acetic acid. Yield: 81 g of compound 30 melting at 209°–222° C.

Compounds 31 and 32 are similarly produced.

Production of compound 29

Stage 1

27.2 g of 4-hydroxyacetophenone are dissolved hot with 8 g of sodium hydroxide in 300 ml of methyl glycol, followed by the addition of 55 g of tetradecyl bromide. The mixture is then boiled for 4 hours and subsequently poured onto water. The deposit precipitated is filtered off under suction and recrystallised from methanol. Yield: 55 g of p-tetradecyloxy acetophenone melting at 56° C.

Stage 2

105 g of this compound are dissolved in 1000 ml of benzene, followed by the dropwise addition at 25° C. of a solution of 15.3 g of bromine in 30 ml of benzene. The reaction mixture is washed with water until neutral and then concentrated. The crystallising residue is recrystallised from methanol.

Yield of ω-bromo-p-tetradecyloxy acetophenone: 33 g, m.p.: 66° C.

Stage 3

5.4 g of KSCN are added to 20.5 g of the above compound in 200 ml of 90% propanol, followed by heating under reflux for 30 minutes to boiling point. The ω-thiocyano-4-tetradecyloxy acetophenone precipitates in crystalline form on cooling and adding water. Recrystallisation from methanol gives 16.5 g melting at 82° C.

Stage 4

36 g of this compound are dissolved hot in 500 ml of glacial acetic acid, followed by the addition of a solution of 3 ml of concentrated sulphuric acid in 30 ml of water. The mixture is then heated for 30 minutes to boiling point. The contents of the flask crystallise on cooling. After filtration under suction, the crystal mass is extracted with petroleum ether. 13 g of compound 29 melting at 116°–118° C. are obtained from the petroleum ether extract.

The compounds according to the invention corresponding to general formula I in which $X=N-R^3$ are also generally produced from the corresponding ω-halogen ketones. Synthesis by one of the following three methods (Y=halogen) is recommended, depending upon the nature of the substituent $R^3$:

1. Where $R^3$=H, alkyl or aryl, the ω-halogen ketone is reacted with the corresponding amine $H_2N-R^3$ to form the ω-amino ketone which is then cyclised with KOCN to form the imidazolinone in accordance with the following reaction equation:

$$R^1-CO-CH_2Y + HNH-R^3 \longrightarrow$$
$$R^1-CO-CH_2-NH-R^3 \cdot HY$$

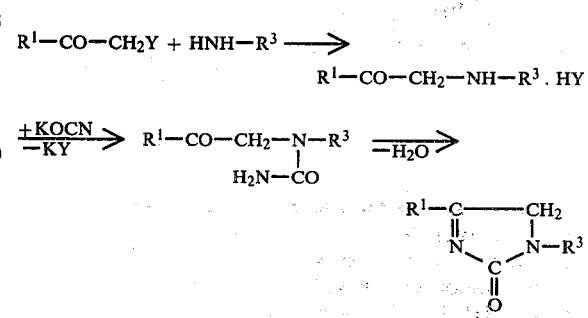

2. For compounds where $R^3=-COOR$, $-SO_2R$, $-CO-R$, the particular parent compound in which $R^3=H$ is used as starting material. It is reacted in basic solvents with the corresponding acid chlorides:

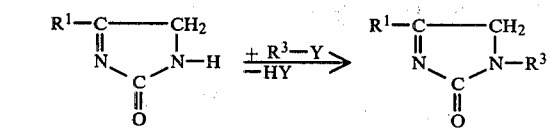

3. For compounds where $R^3=-CN$, synthesis is also possible using the correspondingly substituted urea in accordance with the following reaction scheme:

$$R^1-CO-CH_2-Y +$$

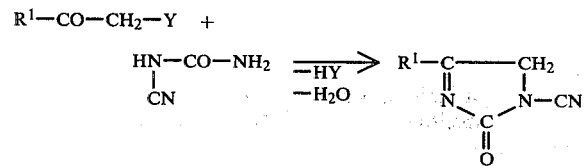

Methods described in the literature may also be used, including for example the methods described in:
Chem. Ber. 99, 2113 (1966);
Chemistry Letters, pages 401–404 (1974), published by The Chemical Society of Japan.

Some typical production methods are described in the following as examples of all three of the above-mentioned procedures.

Production of compound 10

Stage 1

15.5 g of ω-chloroacetophenone are dissolved while stirring in 200 ml of ethanol saturated with ammonia. After standing overnight, the orange-coloured solution is poured onto 500 ml of water. The precipitating oil is separated off and taken up with 80 ml of 20% hydrochloric acid Concentration give 5 g (20% yield) of ω-aminoacetophenone hydrochloride.

Stage 2

17 g of the above compound are dissolved in 100 ml of water, followed by boiling under reflux for 15 minutes following the addition of 33 g of NaOCN. Compound 10 actually precipitates during boiling. Filtration under suction leaves 4 g, corresponding to a yield of 26%, m.p.: 300°–312° C. (decomposition).

Production of compound 12

Stage 1

100 g of ω-bromoacetophenone are dissolved in 600 ml of absolute ethanol, followed by the dropwise addition at 20° C. of 100 g of aniline. On completion of the addition, the ω-anilinoacetophenone formed precipitates in crystalline form. Yield: 62 g=59%; m.p: 97°–99° C.

Stage 2

39 g of the above compound are dissolved warm in 300 ml of glacial acetic acid, followed by the addition of 60 g of NaOCN. After foaming, the mixture is heated for about 1 hour to boiling point and then poured onto water. The deposit precipitating is filtered off under suction and recrystallised from ethanol. Compound 12 is obtained in a yield of 32 g (74%) m.p.: 186°–189° C.

Production of compound 16

Stage 1

10 g of ω-bromoacetophenone are dissolved in 30 ml of hexamethyl phosphoric acid triamide and the resulting solution heated for 4 hours to 60° C. following the addition of 10 g of the sodium salt of sulphanilic acid. The reaction solution is taken up in 200 ml of ethylacetate. The deposit precipitated is filtered off under suction and washed with ethylacetate. The sodium salt of ω-p-sulphonic acid phenylaminoacetophenone is obtained in a yield of 12 g, corresponding to 78%.

Stage 2

18 g of the above compound and 19 g of NaOCN are dissolved warm in 200 ml of glacial acetic acid and the resulting solution is heated under reflux for 1 hour to boiling point. After cooling, hydrogen chloride gas is introduced up to saturation level. Compound 16 precipitates from the orange-red coloured solution in the form of crystals of the free acid. Yield: 6.4 g=35%; m.p. above 300° C.

Production of compound 17

16 g of compound 10 are suspended at room temperature in 150 ml of pyridine, and 14 ml of acetyl chloride are added dropwise to the resulting suspension. After the addition, the mixture is left standing for 1 hour at room temperature, after which it is poured onto 1 liter of water. It is then acidified with 10% hydrochloric acid. 17 g of compound 17 crystallise out. Recrystallisation from methanol gives 10 g=50% of compound 17 melting at 235°–240° C.

Production of compound 38

Stage 1

88 g of p-tetradecyloxy-ω-bromoacetophenone (stage 2 of compound 29) are dissolved in 320 ml of dried chloroform. 30.4 g of urotropin are added at room temperature. The solution undergoes spontaneous heating. It is stirred for 2 hours at room temperature. The chloroform is distilled off and the solid residue is rubbed with acetone. The crystalline deposit is filtered off under suction and washed repeatedly with acetone. The crude product is then introduced into a solution of 140 ml of concentrated sulphuric acid in 100 ml of ethanol, followed by stirring for 24 hours at room temperature. After filtration under suction, the residue is washed with a mixture of ethanol and concentrated hydrochloric acid (7:1), giving 80 g=95% of p-tetradecyloxy-ω-aminoacetophenone hydrochloride melting at 190°–195° C.

Stage 2

80 g of the above compound are dissolved hot in a mixture of 920 ml of ethanol and 380 ml of water. After the addition of a solution of 80 g of KOCN and 300 ml of water, the mixture is heated under reflux for 2 hours to boiling point. After cooling, the product precipitated is filtered off under suction, giving 75 g (95%) of compound 38 melting at 210°–220° C.

Production of compound 40

41 g of 2-tetradecyloxy-ω-bromoacetophenone (produced in accordance with stage 2 of compound 29) (m.p. 69°–70° C.) are dissolved while stirring at 70° C. in 250 ml of dry acetonitrile. 15 g of cyanimidocarboxylic acid ethyl ester in 25 ml of acetonitrile are then added, followed by heating for 4.5 hours to boiling point. After standing for 48 hours, the deposit is filtered off under suction and washed with gasoline heated to 50° C. The collected filtrates are concentrated and the residual oil is taken up with 150 ml of saturated methanolic hydrochloric acid. The deposit precipitating is filtered off under suction, washed with methanol and recrystallised from 350 ml of methanol. 13 g=31% yield of compound 40 melting at 112°–115° C.

Production of compound 45

Stage 1

61.5 g of p-tetradecyloxy-ω-bromoacetophenone (stage 2 of compound 29) are dissolved in 1400 ml of ethanol, followed by the addition of 29.3 g of the sodium salt of sulphanilic acid. After heating under reflux for 2 hours to boiling point, the deposit precipitated is filtered off under suction while still hot. It is then washed with hot ethanol. 40 g=77% of the sodium salt of p-tetradecyloxy-ω-p-sulphonic acid phenylaminoacetophenone.

Stage 2

40 g of the above sodium salt are suspended in 400 ml of boiling glacial acetic acid, followed by the addition in portions of 30.8 g of KOCN. Dissolution gradually occurs with foaming. After heating for 30 minutes to boiling point, the hot reaction solution is filtered off from undissolved constituents. 17 g=40% of compound 45 crystallise out from the filtrate. m.p.: 221°–228° C.

Production of compound 49

16 g (0.1 mole) of compound 10 are suspended with stirring at room temperature in a mixture of 150 ml of dimethyl acetamide and 16 ml of pyridine. 55 g (0.2 mole) of chloroformic acid tetradecyl ester are then added while stirring. A pale red solution is formed, accompanied by spontaneous heating. A thick crystal sludge of compound 49 precipitates slowly during subsequent heating to 60° C. It is filtered off under suction, washed with methanol and with a mixture of 90 ml of methanol and 30 ml of 10% hydrochloric acid and subsequently recrystallised from ethyl acetate. Compound 49 which melts at 166°–171° C. is obtained in a yield of 19 g (47% of the theoretical).

Like conventional white couplers, the compounds according to the invention react with developer oxidation products without at the same time forming permanent dyes. By contrast, unlike conventional white couplers, they are capable of neutralising twice the quantity of developer oxidation product, namely four equivalents. It is therefore possible to develop the same white coupler effects as with conventional white couplers for a smaller load on the layers and with thinner layers.

The compounds according to the invention are particularly suitable for use in colour photographic recording materials which are processed by the chromogenic processing technique or in processing baths therefor. When the compounds according to the invention are diffusion-resistant, they may be incorporated in one or more layers of the colour photographic recording material, for example a photosensitive silver halide emulsion layer or a non-photosensitive binder layer which may be situated adjacent to a photosensitive silver halide emulsion layer, for example as a separating layer between two differently sensitized silver halide emulsion layers. The concentration of diffusion-resistant four-equivalent white coupler compound may be varied within wide limits, for example in a photosensitive silver halide emulsion layer or in a non-photosensitive binder layer between $1\times10^{-3}$ and $500\times10^{-3}$ g/m$^2$. The most favourable concentration in each case may readily be determined by the expert with the aid of a few simple tests.

The concentration of four-equivalent white coupler compounds according to the invention in the processing solutions such as, for example, the developer bath or the bleaching or bleach-fixing bath, depends upon the required effect, the photographic materials used and the emulsions present in them and may again readily be determined with the aid of a few small-scale tests.

The colour photographic recording materials according to the invention in whose processing the four-equivalent white coupler compounds may be used with advantage are preferably multilayer materials which comprise several silver halide emulsion layers or emulsion layer units or different spectral sensitivity. Emulsion layer units are understood to be laminates of two or more silver halide emulsion layers of the same spectral sensitivity.

A colour coupler which is capable of reacting with colour developer oxidation products to form a diffusion-resistant dye is associated with each of the above-mentioned photo-sensitive silver halide emulsion layers or emulsion layer units. The colour couplers are preferably diffusion-resistant and are accommodated in the photosensitive layer itself or in immediate proximity thereto. The colour couplers associated with the two or more component layers of an emulsion layer unit do not necessarily have to be identical. They are merely intended to give the same colour during colour development, normally a colour which is complementary to the colour of the light to which the photosensitive silver halide emulsion layers are sensitive.

Accordingly, at least one diffusion-resistant colour coupler for producing the cyan component of the colour image, generally a coupler based on phenol or α-naphthol, is associated with each of the red-sensitive silver halide emulsion layers. The green-sensitive silver halide emulsion layers each contain at least one diffusion-resistant colour coupler for producing the magenta, component of the colour image, normally a colour coupler based on 5-pyrazolone or indazolone. Finally, the blue-sensitive silver halide emulsion layers each contain at least one diffusion-resistant colour coupler for producing the yellow component of the colour images, generally a colour coupler containing an open-chain keotmethylene group. Large numbers of such colour couplers are known and are described in a number of Patent Specifications. Reference is made here by way of example to the publications "Farbkuppler" by W. Pelz in "Mitteilungen aus den Forschungslaboratorien der Agfa, Leverkusen,/Munchen", Vol. III (1961), page 111, and K. Venkataraman in "The Chemistry of Synthetic Dyes", Vol. 4, 341 to 387, Academic Press (1971).

The colour couplers may be both standard four-equivalent couplers and also two-equivalent couplers in the case of which smaller quantity of silver halide is required for colour formation. It is known that two-equivalent couplers are derived from the four-equivalent couplers in that, in the coupling site, they contain a substituent which is released during the coupling reaction. The two-equivalent couplers which may be used in accordance with the invention include both those which are substantially colourless and also those which have an intense natural colour which disappears during the colour coupling reaction or is replaced by the colour of the image dye produced. The latter couplers may be additionally present in the photosensitive silver halide emulsion layers where they may act as masking couplers for compensating the undesirable secondary densities of the image dyes. The two-equivalent couplers also include the known DIR-couplers, i.e. couplers which in the coupling site contain a releaseable radical which is released as a diffusing development inhibitor on reaction with colour developer oxidation products.

If required, it is possible to use mixtures of colour couplers for adjusting a required colour or a required reactivity. For example, water-soluble colour couplers may be used in combination with hydrophobic water-insoluble couplers.

The colour couplers as well as the four-equivalent white coupler compounds of the present invention may be incorporated in the layers of the colour photographic recording material by the same methods which are also conventionally used for incorporating coupler compounds into hydrophilic binder layers. The methods are essentially determined by whether the compounds to be incorporated are water-soluble or alkali-soluble hydrophilic compounds or hydrophobic compounds.

Whereas hydrophilic compounds are generally added to the emulsion in the form of aqueous alkaline solutions, hydrophobic compounds are best incorporated by one of the known emulsification processes in which, for example, the coupler is dissolved in an organic solvent, optionally in the presence of a high-boiling coupler solvent, and the resulting solution is subsequently dispersed in a gelatin solution. Examples of high-boiling coupler solvents are dibutyl phthalate and tricresyl phosphate. Other coupler solvents are described for example in U.S. Pat. Nos. 2,322,027; 3,689,271; 3,764,336 and 3,765,897.

It is also possible to prepare aqueous dispersions of the hydrophobic couplers and to add them to the particular casting solutions. To this end, aqueous suspensions of the couplers are finely ground, for example by intensive stirring in the presence of sharp sand and/or by applying ultrasonic waves. In this connection, reference is also made to DT-OS 2,609,741 or corresponding U.K. Patent Application 9905/77 filed Mar. 9, 1977.

The intermediate layers which are arranged between the photosensitive silver halide emulsion layers and of which the binder preferably consists of gelatin may contain compounds which are capable of reacting with colour developer oxidation products and which therefore prevent undesirable diffusion of the colour developer oxidation products. In addition to the four-equivalent white coupler compounds according to the invention, examples of compounds such as these are non-diffusing reducing agents, for example hydroquinone derivatives, which do not form any dye remaining in the layers on reaction with the colour developer oxidation products, or colour couplers which give a soluble dye which is washed out of the layers during colour photographic processing. Other suitable compounds for preventing the undesirable diffusion of colour developer oxidation products are described for example in the book entitled "Stabilisation of Photographic Silver Halide Emulsions" by E. J. Birr, The Focal Press, 1st Edition, 1974, pages 116 to 122.

For other suitable additives to the colour photographic recording materials according to the invention or to one of their layers, reference is made to the article in the Journal "Product Licensing Index", Vol. 92, December 1971, pages 107 to 110.

The recording materials according to the invention may be developed with the usual colour developer compounds, particularly with those based on p-phenylene diamine containing a primary amino group, for example 4-amino-N,N-dimethylaniline, 4-amino-N,N-diethylaniline, 4-amino-3-methyl-N,N-diethylaniline, 4-amino-3-methyl-N-methyl-N-($\beta$-methylsulphonamidoethyl)-aniline, 4-amino-N-ethyl-N-($\beta$-hydroxyethyl)aniline, 4-amino-3-methyl-N-ethyl-N-($\beta$-hydroxyethyl)-aniline, 4-amino-3-methyl-N-ethyl-N-($\beta$-methoxyethyl)-aniline, 4-amino-3-methyl-N-ethyl-N-($\beta$-methylsulphonamidoethyl)-aniline, 4-amino-N-butyl-N-($\omega$-sulphobutyl)-aniline and 4-amino-3-methyl-N-isopropyl-N-($\omega$-sulphobutyl)-aniline.

Other suitable colour developers are described for example in J. Amer. Chem. Soc., 73, 3100–3125 (1951).

The invention will now be further described in the following Examples.

EXAMPLE 1

An approximately 8 $\mu$m thick gelatin layer containing a dispersed cyan coupler was cast in accordance with the following recipe onto a transparent film substrate of cellulose acetate provided with an adhesion layer:

16 g of 1-hydroxyl-2-(N-octadecyl)-naphthamide were dissolved at approximately 70° C. in 50 ml of ethylacetate and the resulting solution dispersed in 256 ml of a 5% aqueous gelatin solution heated to about 50° C. to which 10 ml of a 20% aqueous solution of sodium dodecyl benzene sulphonate had been previously added, as wetting agents. The dispersed product was stirred into 300 ml of a 5% gelatin solution and a pH of 6.5 adjusted with a 10% sodium bicarbonate buffer solution following the addition of 80 ml of a 5% aqueous saponin solution and 15 ml of a 2% aqueous muco chloric acid solution as hardener.

This casting solution had a viscosity of approximately 2.5 cP. The solution was dip-cast onto the film substrate at a rate of approximately 5 m/minute.

After drying for 24 hours, this initial casting was coated with a second layer containing a silver halide emulsion and a dispersion of the white coupler to be tested, a coupler/silver ratio of 1:2 being selected. In a O-test (comparison), stearic acid methyl ester was used instead of a white coupler according to the invention and a coupler-free coating was included in the testing of water-soluble types.

The casting solutions were prepared in accordance with the following recipe:
Preparation of the coupler dispersion:

1 mMole of the white coupler was dissolved at around 70° C. in 5 ml of ethylacetate and 0.5 ml of dibutyl phthalate.

The solution was dispersed in 25 ml of a 5% gelatin solution to which 1 ml of a 10% aqueous solution of sodium dodecyl benzene sulphonate had previously been added.

The dispersed product was stirred into 50 ml of a 5% gelatin solution, followed by the addition of 0.75 ml of 2% aqueous muchochloric acid. After the adjustment of a pH-value of 6.5 with a 10% sodium carbonate/bicarbonate buffer solution, 7 g of a silver bromide iodide emulsion ready for casting (340 mg silver nitrate; 0.67 mole % of silver iodide) were added to the coupler dispersion which was then adjusted to a viscosity of approximately 2.5 cP by the addition of water.

Layers with a silver coating of approximately 0.7 g of Ag per square meter were applied at casting rates of around 5 meters per minute. In the case of the coupler soluble in aqueous alkaline solution, the coupler dispersion was replaced by a corresponding coupler solution prepared by dissolving 1 mMole of coupler in 75 ml of a 5% gelatin solution with addition of i mMole of sodium hydroxide, and the coupler solution was added to the silver halide emulsion.

After storage for 48 hours, the test specimens were exposed behind a step wedge and subjected to the following colour development process:

8 minutes' colour development at 20° C. in a solution of
   2.75 g of N,N-diethyl-p-phenylene diamine
   1.2 g of hydroxylamine sulphate
   2.0 g of sodium sulphite, sicc.
   75.0 g of potassium carbonate
   2.5 g of potassium bromide
   2.0 g of sodium hexametaphosphate
   2.0 g of Ethylene diamine tetra acetic acid
   800 ml of water
15 minutes' intermediate rinsing at 20° C.
5 minutes' bleaching at 20° C. in a solution of
   50 g of potassium ferricyanide
   15 g of potassium bromide
   1 g of disodium phosphate
   19 g of monopotassium phosphate
   3 g of ethylene diamine tetraacetic acid
   750 ml of water 5 minutes' rinsing at 20° C.
5 minutes' fixing at 20° in a solution of 200 g of sodium thiosulphate (cryst.)
ad 1000 ml of water
10 minutes' final rinsing at 20° C.

Thereafter the colour density of the developed step wedges was measured behind a red filter at a certain exposure stage, the exposure stage selected being that of the highest exposure intensity. The reduced colour density of the white-coupler-containing test specimens in comparison with the standard is a measure of the effectiveness of the couplers.

The results shown in Table 1 were obtained in this way:

Table 1

| Coupler No. | D/behind red filter | Ag/m$^2$ |
|---|---|---|
| O-test with stearic acid methyl ester | 0.58 | 0.73 |
| 29 | 0.29 | 0.72 |
| 31 | 0.34 | 0.74 |
| 34 | 0.27 | 0.76 |
| 40 | 0.42 | 0.73 |
| O-test without white coupler | 0.52 | 0.70 |
| 45 | 0.21 | 0.68 |
| 46 | 0.30 | 0.72 |
| 47 | 0.24 | 0.71 |

EXAMPLE 2

The effectiveness of the compounds according to the invention when used in a bleach-fixing bath is illustrated by the following comparison:

Unexposed test strips of a standard commercial-grade Agfa-Color paper were fixed, rinsed and dried. The strips free from silver halide were immersed for 1 minute in a developer of the following composition:

| | |
|---|---|
| 2-amino-5-(N-ethyl-N-$\beta$-methane-sulphonamidoethylamino)-toluene | 5 g |
| potassium carbonate | 35 g |
| sodium sulphate, sicc. | 3 g |
| Hydroxylamine sulphate | 2 g |
| potassium bromide | 0.6 g |
| Make up with water to 1000 ml. | |

The samples were freed from excess developer liquid by means of a stripper and then immersed for 5 minutes in a bleach-fixing bath of the following composition:

| | |
|---|---|
| Fe$^{III}$-complex of ethylene diamine tetra acetic acid | 35 g |
| Ethylene diamine tetraacetic acid (tetra-sodium salt) | 15 g |
| sodium sulphate, sicc. | 8 g |
| Ammonium thiosulphate | 100 g |
| Make up with water to 1000 ml; pH: 7.2 | |

Three baths were used for comparison:
Bath 1, no addition
Bath 2 containing 1.8 g of compound 16
Bath 3 containing 2.5 g of compound 20.

After the treatment, the test specimens were exposed to air for 5 minutes after excess bleach-fixing bath had been removed by means of a stripper. After rinsing with water for 10 minutes and drying, the colour fog was measured.

The following Table shows the effectiveness of the compounds according to the invention:

Table 2

| Compound | Measured density |
|---|---|
| none | 0.24 yellow |
| | 0.20 magenta |
| 16 | 0.14 yellow |
| | 0.13 magenta |
| 20 | 0.18 yellow |
| | 0.15 magenta |

EXAMPLE 3

A colour photographic material was produced by applying a colour-coupler-containing red-sensitised silver bromide iodide emulsion of medium sensitivity to a support layer of cellulose acetate provided with an adhesion layer.

Coupler: 1-hydroxy-2-[$\gamma$-(2,4-di-tert.-amylphenoxy)-propyl]naphthamide (emulsified with dibutyl phthalate)

Silver coating: 1.5 g of silver nitrate per m$^2$
Ratio of silver to coupler: 6:1.

Processing was carried out in the following colour reversal processing cycle at a temperature of 30° C. (all baths):

1. initial development 6.5 minutes
2. stopping 2 minutes
3. rinsing 2 minutes
4. second exposure 2 minutes
5. colour reversal development 10 minutes
6. stopping 2 minutes
7. rinsing 2 minutes
8. bleaching 4 minutes
9. rinsing 2 minutes
10. fixing 2 minutes
11. final rinsing 2 minutes.

The baths had the following composition (quantities per 1000 ml; the pH-value was measured at 20° C.).

First developer bath (1)

Trisodium ethylene diamine tetraacetic acid 2 g
Sodium carbonate 28 g
Sodium sulphite 50 g.
Hydroquinone 6 g
4-methyl phenidone 0.3 g
Potassium thiocyanate 2.5 g
Potassium bromide 2 g
Potassium iodide 15 mg
Sodium hydrogen carbonate 6 g
pH: 10.1

Stop bath (2 and 6)

Sodium acetate 10 g
Glacial acetic acid (96%) 20 ml
pH: 4.1

Reversal colour developer bath (5)

Trisodium ethylene diamine tetraacetic acid 2 g
Trisodium phosphate 20 g
Sodium sulphite 5 g
4-amino-3-methyl-N-ethyl-N-($\beta$-hydroxyethyl)-aniline sulphate monohydrate 6 g
Potassium bromide 2 g Potassium iodide 35 mg
pH: 11.7

Bleaching bath (8)

Sodium hexametaphosphate 4 g
Potassium ferricyanide 66 g
Potassium bromide 20 g
Monopotassium phosphate 5 g
pH: 5.0

Fixing bath (10)

Trisodium ethylene diamine tetraacetic acid 1 g
Ammonium thiosulphate 133 g
Sodium sulphite 10 g
pH: 7.3

The white couplers (competitive couplers) to be tested were added to the reversal colour developer bath (5) in a quantity of 0.01 mole.

A first sample of the material described above was processed in the above-defined processing cycle, no white coupler being added to the reversal colour developer bath (sample A—comparison).

In the processing of a second sample, the colour reversal developer bath contained 1.77 g of citrazinic acid (sample B—comparison).

In the processing of a third sample, the reversal colour developer bath contained 1.55 g of compound No. 2 (sample C—according to the invention).

The results are set out in Table 3 below:

Table 3

| Sample | White coupler [g/l] | | $D_{max}$ behind red filter [units] | [%] (sample A = 100%) |
|---|---|---|---|---|
| A | — | — | 2.64 | 100 |
| B | citrazinic acid | 1.55 | 2.00 | 76 |
| C | No. 2 | 1.77 | 1.76 | 67 |

EXAMPLE 4

A colour photographic material was produced in the same way as in Example 3, except that a green-sensitised silver bromide iodide emulsion and a magenta coupler were used.
Coupler: 1-(2,4,6-trichlorophenyl)-3-[3-(2,4-di-tert.-amylphenoxy)-acetamido]-benzamido-5-pyrazolone (emulsified with dibutyl phthalate)
Silver coating: 2.8 g of silver nitrate per square meter
Ratio of silver to colour coupler: 9:1.

Processing was carried out in the same way as described in Example 3.

In the processing of a first sample, the colour reversal developer bath did not contain a white coupler (sample D—comparison).

In the processing of a second sample, the colour reversal developer bath contained 1.55 g of citrazinic acid (sample E—comparison).

In the processing of a third sample, the colour reversal developer bath contained 3.16 g of compound No. 16 (sample F—according to the invention).

The results are shown in Table 4 below:

Table 4

| Sample | White coupler [g/l] | | $D_{max}$ behind green filter [units] | [%] |
|---|---|---|---|---|
| D | — | — | 4.02 | 100 |
| E | citrazinic acid | 1.55 | 3.00 | 75 |
| F | No. 16 | 3.16 | 1.36 | 34 |

EXAMPLE 5

A colour photographic material was produced by coating the following three layers onto a support layer of cellulose acetate provided with an adhesion layer.
first layer: as described in example 1
second layer: a gelatin layer 1 μm thick
third layer: a highly sensitive silver bromide gelatine emulsion;

This was sample A; the casting solution for the second layer was made as follows:

50 ml of a 5% aqueous gelatin solution were diluted with 150 ml of water.

In a second sample (sample B) the second layer 1 μm thick) contained a conventional white coupler of the following formula

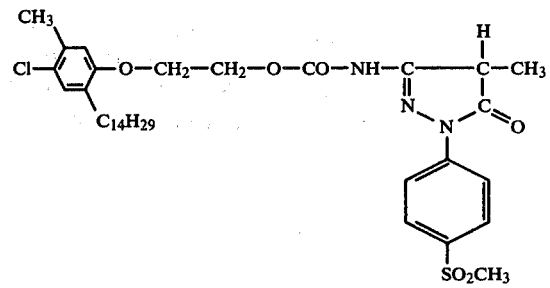

(described in DT-OS 1 909 067; coupler II)

The casting solution was made up as follows: 1 mmole of the coupler was dispersed in 50 ml of a 5% aqueous gelatin solution; the dispersion was diluted with 150 ml of water.

In a third sample (sample C) the second layer (1 μm thick) contained the white coupler compound 40 of the invention. The casting solution for the second layer was made up in the same way as that of sample B.

The three samples were exposed behind a step wedge and processed in one of the negative development processings I, II and III respectively.

Processing I is that described in example 1. Processing II is the same as processing I except that for colour development the developer bath of example 2 (without white coupler) was used. Processing III is the same as processing I except that for colour development the colour developer bath (5) of example 3 was used.

The white coupler activity was estimated from the colour density measured in the three samples behind a red colour filter as shown in the following table.

Table 5

| Sample | Density measured behind red filter after Processing | | |
|---|---|---|---|
| | I | II | III |
| A | 0,73 | 0,83 | 0,63 |
| B | 0,24 | 0,18 | 0,22 |
| C | 0,20 | 0,14 | 0,14 |

We claim:
1. A process for the production of colored images by the chromogenic development of an imagewise exposed color photographic material comprising at least one silver halide emulsion layer with which a non-diffusing color coupler is associated, which process includes the processing steps of color development, bleaching and fixing, wherein the improvement comprises the development step and/or the bleaching step is/are carried out in the presence of a compound capable of reacting with color developer oxidation products with the consumption of four oxidation equivalents to form colorless end products, said compound corresponding to formula I or its tautomeric form Ia:

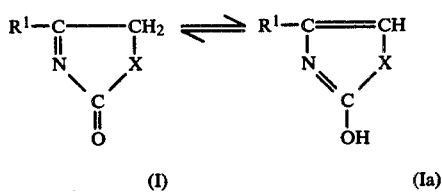

in which
R$^1$ represents an alkyl group from 1 to 18 carbon atoms, a phenyl group, a naphthyl group, a photographically inert heterocyclic radical selected from the group consisting of pyridyl, thienyl, thiazolyl, furanyl and indole radicals, attached through a ring carbon atom X represents —S— or —NR$^3$—
  where R$^3$ represents hydrogen, an alkyl group from 1 to 18 carbon atoms, a phenyl group, a naphthyl group, a photographically inert heterocyclic radical selected from the group consisting of pyridyl, thinyl, thiazolyl, furanyl and indole radicals, attached through a ring carbon atom or an electron-attaching substituent selected from the group consisting of —CN, alkoxy carbonyl, carbamoyl, sulfamoyl, alkyl sulfonyl and aryl sulfonyl radicals.

2. A process as claimed in claim 1, wherein R$^3$ represents a group corresponding to the formula

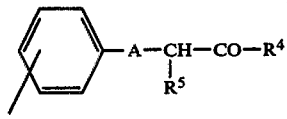

in which A represents a single chemical bond or —O—, —S— or —NR'— (R'=hydrogen or alkyl), R$^4$ represents hydroxyl, alkoxy, alkylamino or arylamino and R$^5$ represents hydrogen or alkyl with 1 to 16 carbon atoms.

* * * * *